(12) United States Patent
Kumamoto et al.

(10) Patent No.: US 7,353,820 B2
(45) Date of Patent: Apr. 8, 2008

(54) WARMING DEVICE

(75) Inventors: Yoshiaki Kumamoto, Haga-gun (JP); Masataka Ishikawa, Haga-gun (JP); Takao Orii, Sumida-ku (JP); Christine Hall, Cincinnati, OH (US); Jill Kathleen Lynch, Cincinnati, OH (US)

(73) Assignee: KAO Corporation, Tokyo (JP)

(*) Notice: Subject to any disclaimer, the term of this patent is extended or adjusted under 35 U.S.C. 154(b) by 153 days.

(21) Appl. No.: 10/873,225

(22) Filed: Jun. 23, 2004

(65) Prior Publication Data
US 2005/0028806 A1 Feb. 10, 2005

Related U.S. Application Data

(60) Provisional application No. 60/483,100, filed on Jun. 30, 2003.

(51) Int. Cl.
*F24J 1/00* (2006.01)
*A61F 7/00* (2006.01)

(52) U.S. Cl. ............ 126/204; 126/263.01; 44/251

(58) Field of Classification Search .......... 126/204, 126/263.01, 263.02; 607/109, 111, 114, 607/112, 108, 96; 165/46; 44/250–253, 44/901, 902
See application file for complete search history.

(56) References Cited

U.S. PATENT DOCUMENTS

RE32,026 E * 11/1985 Yamashita et al. ..... 126/263.02
4,573,447 A * 3/1986 Thrash et al. ............... 607/111
5,318,844 A * 6/1994 Brandon ..................... 428/357
5,425,975 A * 6/1995 Koiso et al. ................ 126/204
5,662,624 A * 9/1997 Sundstrom et al. ......... 604/291
2005/0000827 A1 1/2005 Matsui et al.
2005/0028806 A1 2/2005 Kumamoto et al.
2006/0151136 A1 7/2006 Kumamoto et al.

FOREIGN PATENT DOCUMENTS

| JP | 1-223960 A | * | 9/1989 |
| JP | 3-15463 A | * | 1/1991 |
| JP | 9-154869 A | * | 6/1997 |
| JP | 2003-332 | | 1/2003 |

OTHER PUBLICATIONS

Klungness, John H., Marguerite Sykes, Aziz Ahmed, Said AbuBakr, "Preventing Loss and Restoring Water retention Values to Pulp by Fiber Loading." 2000 TAPPI recycling Symposium: vol. Two, Washington, D.C., Mar. 5-8, 2000.*
U.S. Appl. No. 10/556,136, filed Nov. 9, 2005, Kumamoto, et al.
U.S. Appl. No. 10/566,471, filed Jan. 31, 2006, Kumamoto, et al.

* cited by examiner

*Primary Examiner*—Josiah C. Cocks
(74) *Attorney, Agent, or Firm*—Oblon, Spivak, McClelland, Maier & Neustadt, P.C.

(57) ABSTRACT

A warming device consisting essentially of a heat generating main body comprising a heat generating element and an air-permeable holding member having the heat generating element enclosed therein. The warming device has a receiving part for receiving a part of a body being inserted. The heat generating element comprises a sheet which contains an oxidizable metal, a moisture-retaining agent, and a fibrous material and is prepared by papermaking.

9 Claims, 7 Drawing Sheets

WARMING DEVICE

BACKGROUND OF THE INVENTION

The present invention relates to a warming device utilizing heat generation accompanying oxidation of an oxidizable metal with oxygen in air.

Known techniques pertinent to warming devices utilizing heat generation accompanying oxidation of an oxidizable metal powder with air oxygen include the warming tool described in JP-A-2003-332.

The warming tool disclosed comprises a cap-shaped base sheet which is put on a head and a plurality of heat generating elements attached to the base sheet, the heat generating elements each comprising an air permeable flat bag containing heat generating powder.

Because the heat generating elements used in this warming tool are thick, a thinner warming device has been desired. Because the heat generating elements lose flexibility as the heat generating powder becomes harder, a warming device having excellent in flexibility and thereby providing a good fit has been desired. Furthermore, since the thick heat generating elements being attached to the base sheet limit the freedom of design, a warming device having broader applications has been demanded.

SUMMARY OF THE INVENTION

An object of the present invention is to provide a warming device which is thin, flexible, conformable to a part of a wearer's body, and applicable to a diversity of uses.

The present invention provides a warming device which consists essentially of a heat generating main body comprising a heat generating element and an air-permeable holding member having the heat generating element enclosed therein and has a receiving part for receiving a part of a body being inserted, the heat generating element comprising a sheet which contains an oxidizable metal, a moisture-retaining agent, and a fibrous material and is prepared by papermaking.

BRIEF DESCRIPTION OF THE DRAWINGS

The present invention will be more particularly described with reference to the accompanying drawings, in which:

FIG. 6 schematically shows a fourth embodiment of the warming device according to the present invention, in which (a) is a half cross-sectional view, and (b) is a side view.

DETAILED DESCRIPTION OF THE PREFERRED EMBODIMENTS

The present invention will be described in greater detail with reference to the accompanying drawings.

Figure 1:
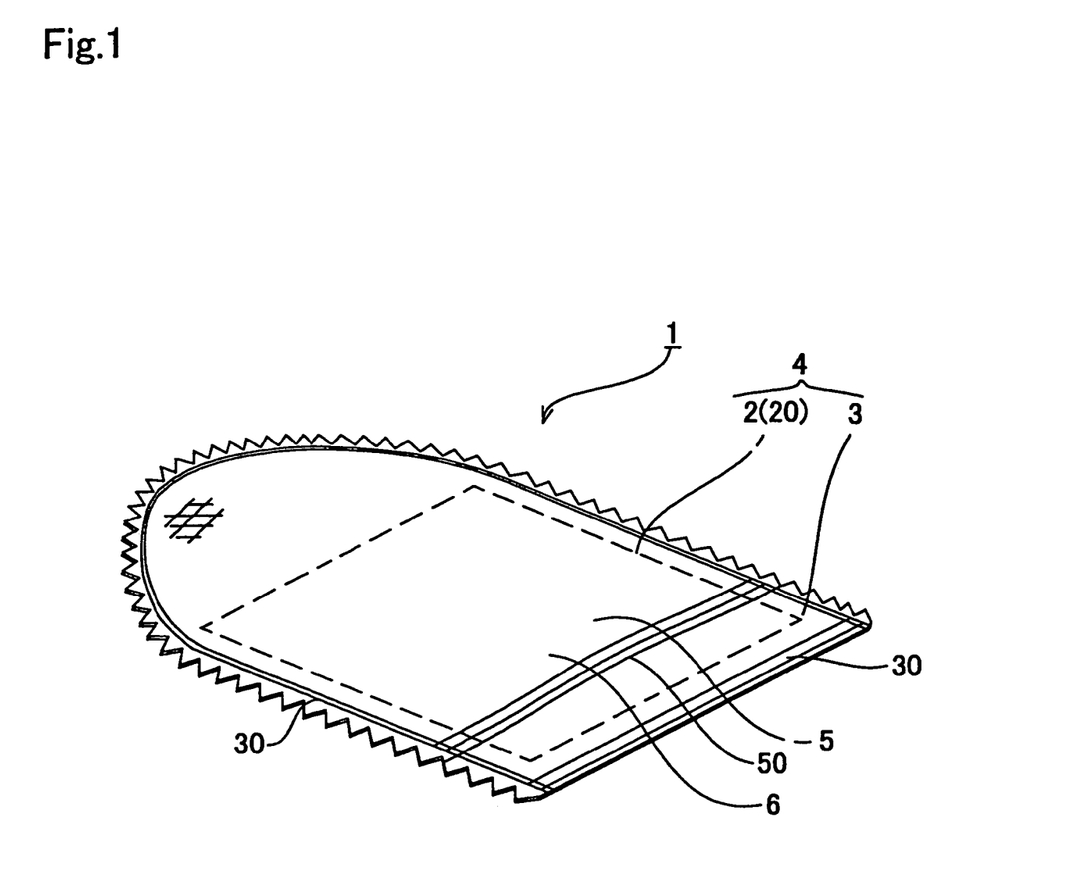
FIG. 1 is a perspective schematically illustrating a first embodiment of the warming device according to the present invention.
Figure 2:
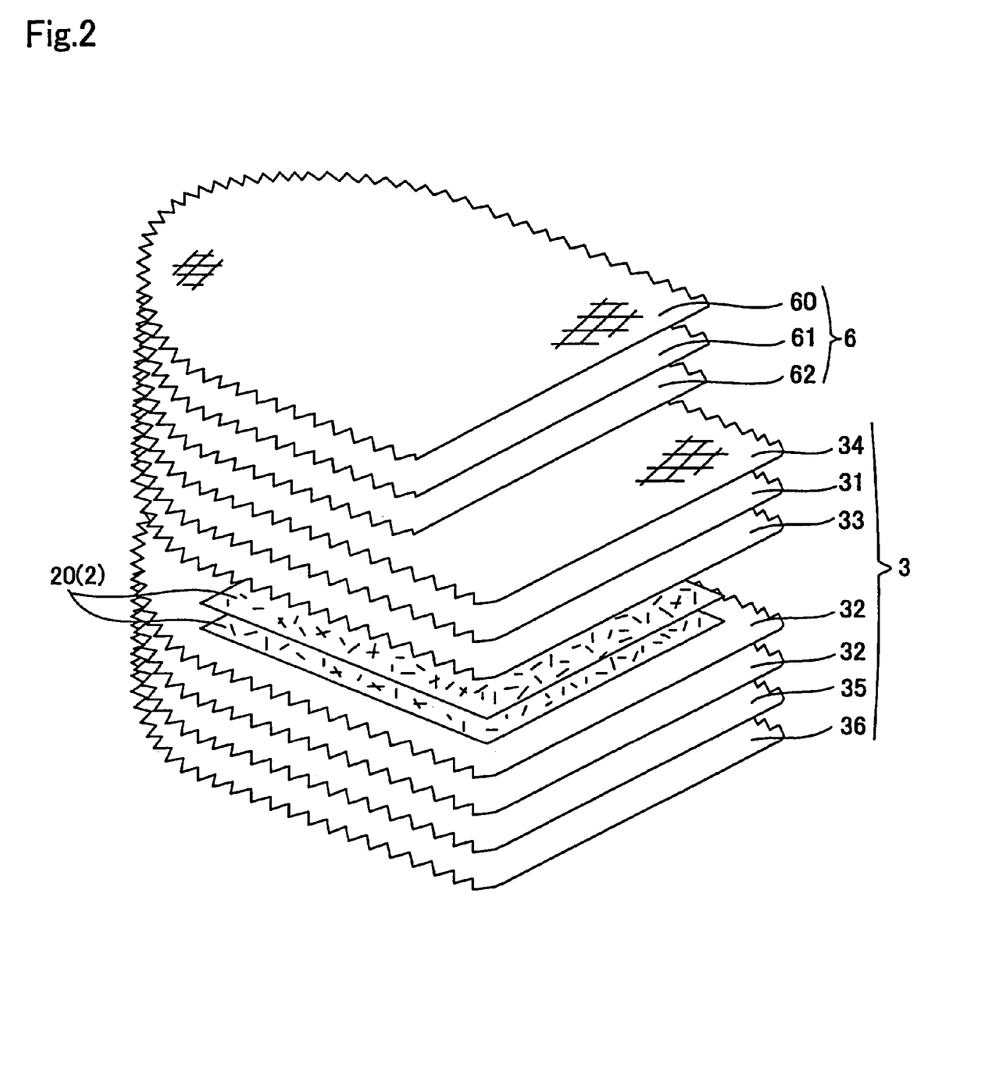
FIG. 2 is an exploded perspective schematically illustrating the warming device of the first embodiment.

FIGS. 1 and 2 show a first embodiment of the present invention, in which the warming device is shaped into a mitten. In these figures numeral 1 indicates the warming device.

As illustrated in FIG. 1, the warming device 1 consists essentially of a heat generating main body 4 which comprises a heat generating element 2 and an air-permeable holding member 3 having the heat generating element 2 enclosed therein. The warming device 1 has a receiving part 5 for receiving a part of a body being inserted. The warming device 1 has an receiving part-forming member 6 bonded to the upper side of the heat generating main body 4 to form the receiving part 5 having an insertion opening 50 on the outer side of the heat generating main body 4.

The heat generating element 2 is composed of a sheet 20 which is prepared by papermaking and contains an oxidizable metal, a moisture-retaining agent, and a fibrous material. A sheet 20 which does not contain an electrolyte component is called a heat generating intermediate sheet 20, and a sheet 20 containing an electrolyte component (hereinafter described) and water is called a heat generating sheet 20. The heat generating element 2 of the warming device 1 according to the first embodiment consists of two heat generating sheets 20 (see FIG. 2).

The heat generating intermediate sheet 20 preferably contains at least 50% by weight, particularly 70% by weight or more, especially 80% by weight or more, of components other than the above-described fibrous material. Where the components other than the fibrous material is 50% by weight or more, the heat generating element can raise its temperature to a degree that is felt hot on touching with fingers, etc. While it is desirable that the proportion of the components other than the fibrous material be increased as much as possible, the upper limit would be 98% by weight for securing sufficient strength to maintain fabricability of the heat generating intermediate sheet 20.

The proportion of the components other than the fibrous materials of the heat generating intermediate sheet 20 is calculated as follows, the weight of the solids content of the slurry: Ms
the proportion of the fibrous materials of the solids content of the slurry: a(%)
the weight of the dried heat generating intermediate sheet: Mh
the proportion of the components other than the fibrous materials of the heat generating intermediate sheet: b(%)

$$b=(Mh/Ms)\times(100-a)$$

The oxidizable metal for use in the invention can be of any kind that is commonly employed in this type of heat generating elements. The oxidizable metal is preferably in the form of powder or fiber from the standpoint of ease in handling and molding capabilities.

Oxidizable metals in the form of powder include iron powder, aluminum powder, zinc powder, manganese powder, magnesium powder, and calcium powder. Iron powder is preferred among them in view of ease in handling, safety, and competitive production cost. Taking fixability onto the fibrous material and reaction controllability into consideration, the oxidizable metal powder preferably has a particle size of 0.1 to 300 µm. The term "particle size" as used herein means a maximum length of a powder particle or an average particle size measured by dynamic light scattering method, a laser diffraction method, and the like. It is still preferred to use powder containing at least 50% by weight of particles having a particle size of 0.1 to 150 µm.

Oxidizable metals in the form of fiber include steel fiber, aluminum fiber, and magnesium fiber. Steel fiber and aluminum fiber are preferred for their ease in handling, safety, and low cost. The fibrous oxidizable metal preferably has a length of 0.1 to 50 mm and a thickness of 1 to 1000 μm, from the viewpoint of molding capabilities, mechanical strength and surface smoothness of the resulting sheet, and heat generating performance.

The heat generating intermediate sheet 20 preferably contains 10 to 95% by weight, particularly 30 to 80% by weight, of the oxidizable metal. With the oxidizable metal content being 10% by weight or more, the heat generating sheet 20 can generate heat to such a degree that is felt hot on touching with fingers, etc. Besides, the sufficient proportion of the fibrous material and a binding component (e.g., a flocculant, hereinafter described) results in making the heat generating sheet hard enough and comfortable in use. Where the oxidizable metal content is 95% by weight or less, on the other hand, an oxide layer (e.g., of the oxidizable metal) would not be formed on the surface of the heat generating sheet 20, which will retain air permeability of the sheet. As a result, the reaction proceeds inside of the sheet to increase temperature. Further, Expansion and setting of the oxidizable metal due to the oxidation reaction tends not to make the sheet harder and the heat generation is sustained. Besides, water is supplied by the moisture-retaining agent sufficiently and the falling of oxidizable metal from the sheet is suppressed. Furthermore, the sufficient proportion of the fibrous material and the binding component of the heat generating sheet 20 can result in good mechanical strength, such as flexural strength and tensile strength. The oxidizable metal content in the heat generating sheet 20 can be measured by ash determination in accordance with JIS P8128. An iron content can also be determined by vibrating sample magnetization measurement making use of the magnetization phenomenon in an external magnetic field.

The moisture-retaining agent for use in the invention can be of any kind that is customarily employed in heat generating elements. The moisture-retaining agent has a water retaining function combined with a function as an agent for retaining and supplying oxygen to the oxidizable metal. Such a moisture-retaining agent includes activated carbon (including coconut shell charcoal, charcoal powder, bituminous coal, peat, and lignite), carbon black, acetylene black, graphite, zeolite, pearlite, vermiculite, silica, cancrinite, and fluorite. Preferred of them is activated carbon in view of its water retaining capability, oxygen feeding capability, and catalyzing ability. The moisture-retaining agent preferably has a powder form with a particle size ranging 0.1 to 500 μm for providing effective contact with the oxidizable metal. It is still preferred to use powder containing at least 50% by weight of particles having a particle size of 0.1 to 200 μm. Moisture-retaining agents of other forms are also usable. For example, those of fibrous form such as activated carbon fiber can be used.

The heat generating intermediate sheet 20 preferably contains 0.5 to 60% by weight, particularly 1 to 50% by weight, of the moisture-retaining agent. A moisture-retaining agent content of 0.5% by weight or more tends to retain in the heat generating sheet 20 a sufficient amount of water for making the oxidizable metal continue being oxidized to generate heat to such a degree that can be felt warmer than a human body temperature. Besides, the air permeability of the heat generating sheet 20 would be sufficient to result in good oxygen supply, leading to good heat generation efficiency. Where the moisture-retaining agent content is 60% by weight or less, the heat generating sheet 20 will have preferable heat capacity for the quantity of generated heat. It can follow that the rise in temperature is sufficient for a user to feel warmed. The moisture-retaining agent may sufficiently retain in the sheet. Moreover, the sufficient proportion of the fibrous material and the binding component results in good mechanical strength such as flexural strength and tensile strength.

The fibrous material which can used in the present invention includes natural fibers, synthetic fibers, metal fibers, carbon fiber, and glass fiber. The natural fibers include plant fibers, such as cotton, kapok fiber, wood pulp, non-wood pulp, peanut protein fiber, corn protein fiber, soybean protein fiber, mannan fiber, rubber fiber, hemp, Manila fiber, sisal fiber, New Zealand flax, Luo Buma, coconut, rush, and straw; animal fibers, such as wool, goat hair (including mohair and cashmere), alpaca, angora, camel, vicuna, silk, down, small feather, alginate fiber, chitin fiber, and casein fiber; and mineral fibers, such as asbestos. The synthetic fibers include semi-synthetic ones, such as cellulose diacetate fiber, cellulose triacetate fiber, oxidized cellulose acetate fiber, promix fiber, chlorinated rubber, and rubber hydrochloride. Useful synthetic fibers additionally include single-component fibers made of polyolefin (e.g., high-density polyethylene, medium-density polyethylene, low-density polyethylene or polypropylene), polyester, polyvinylidene chloride, starch, polyvinyl alcohol or polyvinyl acetate, a copolymer comprising monomers of these homopolymers, or a modified product of the homo- or copolymer; and core/sheath conjugate fibers having the above-recited resin component as a sheath. Of these synthetic fibers, polyolefin fibers and modified polyester fibers are preferably used for high bonding strength between individual fibers, high ability to form a three-dimensional network structure on fusion bonding of individual fibers, and lower melting point than the ignition point of pulp fiber. Synthetic fibers of polymers having branches, such as branched polyolefin fibers, are also preferred for securing good fixation of the oxidizable metal and the moisture-retaining agent. The above-recited fibrous materials can be used either individually or as a combination of two or more thereof. Recycled products of these fibrous materials are also useful. Among these fibrous materials particularly preferred are wood pulp and cotton in view of their fixing capabilities for the oxidizable metal and the moisture-retaining agent, flexibility of the resulting sheet, oxygen permeability of the resulting sheet owing to the presence of interstices among fibers, and the cost of production.

It is preferred for the fibrous material to have a CSF (Canadian Standard Freeness) of 600 ml or less, particularly 450 ml or less. Fibrous materials having a freeness of 600 ml or less shows good ability to fix and hold the oxidizable metal, the moisture-retaining agent, etc., and the resulting sheet tends to has predetermined amount of these components, which results in good heat generation. The resulting sheet also has evenness of sheet thickness. Further, fall-off of the oxidizable metal and the moisture-retaining agent from the sheet due to the poor fixing and holding ability of the low-freeness fibrous material is suppressed, and sufficient entanglement between the fibrous material and these components and bonding strength relying on hydrogen bonding is obtained. As a result, the sheet would have good mechanical strength such as flexural strength and tensile strength, and good fabricability.

It is desirable for the fibrous material to have as low a CSF as possible. In general papermaking using pulp fiber as a sole fibrous material and small contents of other components, a CSF 100 ml or more means freeness making dewatering good. It can follow that the resulting sheet has thickness evenness and seldom has molding defects such as burst of blisters on drying. In the present invention, on the other hand, the presence of the components other than the fibrous material in high proportions contributes to optimization of freeness and provides a heat generating sheet with a uniform thickness. A lower CSF indicates a higher fibril content, and a higher fibril content secures better fixation of the components other than the fibrous material on the fibrous material, which results in high sheet strength. The CSF of a fibrous material can be controlled by the degree of beating or blending fibers different in CSF.

The fibrous material preferably has a negative zeta potential. "Zeta potential" is an apparent potential at the shear plane (slipping plane) separating a charged particle and a thin layer of a liquid, which can be determined by streaming potential measurement or electrophoresis measurement. A fibrous material having a negative zeta potential has good capability of fixing and holding the oxidizable metal, the moisture-retaining agent, etc. and tends to maintain predetermined amounts of these other components, resulting in good heat generating performance. Suppressed amounts of these components would be lost with waste water, which is not adversely affect the productivity and the environmental preservation.

The fibrous material preferably has an average length of 0.1 to 50 mm, particularly 0.2 to 20 mm. The fibrous materials have such an average length tend to secure sufficient mechanical strength (such as flexural strength and tensile strength) of the heat generating sheet 20, and will not make the fibrous layer dense. The heat generating sheet 20 will have sufficient air permeability, i.e., good oxygen supply, resulting in good heat generation. The fibrous materials have such an average length disperse uniformly in a heat generating sheet 20, which results in a uniform mechanical strength or uniform sheet thickness. In addition, the fiber distance is not expanded and the capability of holding the components such as the oxidizable metal, the moisture-retaining agent, and the like is held, resulting in preventing from fall off of the components.

The fibrous material content in the heat generating intermediate sheet 20 is preferably 2 to 50% by weight, more preferably 5 to 40% by weight. Where the content is 2% by weight or more, the effect for preventing the oxidizable metal and the moisture-retaining agent from falling off is sufficiently obtained, and the heat generating sheet 20 does not tend to be very brittle. If the fibrous material content is 50% by weight or less, the heat generating sheet 20 has a preferable heat capacity for the amount of heat generated, and a sufficient rise in temperature results. Furthermore, as the proportion of the oxidizable metal, the moisture-retaining agent, etc. in the heat generating sheet 20 is retained, a desired heat generating performance is obtained.

The heat generating intermediate sheet 20 can contain a flocculant as hereinafter described. If desired, the heat generating sheet 20 can contain additives commonly used in papermaking, such as sizes, colorants, strengthening agents, yield improvers, loading materials, thickeners, pH control agents, and bulking agents, with no particular limitation. The amounts of the additives to be added can be selected arbitrarily according to the kinds.

The electrolyte to be added in the heat generating sheet 20 can be of any kind chosen from those commonly used in this type of heat generating elements. Examples of useful electrolytes include sulfates, carbonates, chlorides or hydroxides of alkali metals, alkaline earth metals or heavy metals. Preferred of them are chlorides, such as sodium chloride, potassium chloride, magnesium chloride, and iron (I) or (II) chloride, for their electrical conductivity, chemical stability, and production cost. These electrolytes can be used either individually or as a combination of two or more thereof.

The electrolyte is suitably added in an amount of 0.5 to 30% by weight, particularly 1 to 25% by weight, based on the water content of the heat generating sheet 20. Where the amount of the electrolyte is 0.5% by weight or more based on water, the oxidation reaction of the resulting heat generating sheet 20 tends to be sufficient, or the water content necessary to maintain the requisite amount of the electrolyte for heat generation should be suppressed, which can result in a sufficient temperature rise. If the amount of the electrolyte based on the water content is 30% by weight or less, the precipitation of the excess electrolyte may be suppressed, resulting in good air permeability of the heat generating sheet 20. Furthermore, the water content in the heat generating sheet 20 necessary to provide a sufficient amount of the electrolyte for heat generation tends to be sufficient to supply water to the oxidizable metal, resulting in good heat generating performance and uniform distribution of the electrolyte throughout the heat generating sheet 20.

The electrolyte is suitably added in an amount of 0.05 to 20% by weight, particularly 0.1 to 10% by weight, based on the heat generating sheet 20. Where the amount of the electrolyte is 0.05% by weight or more based on the heat generating sheet 20, the oxidation reaction of the resulting heat generating sheet 20 tends to be sufficient, which can result in the good heat generating performance. If the amount of the electrolyte based on the heat generating sheet 20 is 20% by weight or less, the precipitation of the excess electrolyte may be suppressed, resulting in good heat generating performance.

The water content of the heat generating sheet 20 is preferably 10 to 80% by weight, more preferably 20 to 60% by weight. Where the water content is 10% by weight or more, desired amount of water to continue the oxidation reaction is retained and the reaction proceeds efficiently. Moreover, the sufficient amount of water may be uniformly distributed throughout the heat generating sheet 20, resulting in a uniform heat generation. Where the water content is 80% by weight or less, the heat generating sheet 20 will have a preferable heat capacity for the amount of heat generated. It can follow that the rise in temperature is sufficient, the air permeability of the heat generating sheet 20 is retained, and the sheet has a good heat generating performance, shape retention or mechanical strength.

The thickness of the heat generating intermediate sheet 20 is preferably 0.08 to 1.2 mm, more preferably 0.1 to 0.6 mm. A heat generating intermediate sheet 20 with a thickness of 0.08 mm or more has good heat generating performance, sufficient mechanical strength, and good fixing and holding capability for the oxidizable metal, the moisture retaining agent, etc. The sheet with uniform thickness and composition is obtained. And the sheet is liable to break due to pinhole development, leading to sufficient productivity and good fabricability. A sheet with a thickness of 1.2 mm or less has a sufficient folding strength and hardly undergoes brittle fracture. The sheet with such a thickness is likely to be hard enough to provide a good fit with comfort particularly when applied to a bending and stretching part of a body, such as elbows, knees, and the face. In addition, the sheet with such thickness does not need a long time for papermaking and drying, which can result in not only good productivity but sufficient heat generating performance or good fabricability (i.e., liability to breakage of fracture).

The basis weight of the heat generating intermediate sheet 20 is preferably 10 to 1000 g/m$^2$, more preferably 50 to 600 g/m². In using, for example, an oxidizable metal having a high specific gravity, it tends to be able to stably form a sheet having a basis weight of 10 g/m² or more. A sheet with a basis weight of 1000 g/m² or less tends to feel so light as to give comfort to a user and have good productivity or workability.

It is preferred for the heat generating intermediate sheet 20 to have a breaking length of 100 to 4000 m, particularly 200 to 3000 m. Where the breaking length is 100 m or more, it can form the sheet in a stable manner without breaks or tears; the resulting sheet can be stably fabricated due to liability to breaking or tearing; and the final product is apt to sufficient in elasticity, crumble hardly, and give comfort to a user. A heat generating intermediate sheet 20 with a breaking length of 4000 m or less, which does not contain large amounts of the fibrous material and the binding component, tends to be hard and rigid enough, and to have good heat generating performance. The breaking length of a heat generating intermediate sheet is measured as follows.

Measurement of Breaking Length:

A 15 mm wide and 150 mm long specimen cut out of a heat generating intermediate sheet 20 is subjected to a tensile test at an initial gauge length of 100 mm and a pulling speed of 20 mm/min in accordance with JIS P8113. A breaking length is calculated according to equation:

Breaking length $(m)=(1/9.8)\times[$(tensile strength $(N/m)]\times 10^6/$[basis weight $(g/m^2)$]

The maximum temperature reached by the heat generating sheet 20 on heat generation is preferably 30 to 100° C., more preferably 35 to 90° C. This temperature is measured as follows.

Measurement of Maximum Temperature Reached by Heat Generating Sheet on Heat Generation:

A 50 mm side square test piece cut out of a heat generating sheet is enveloped and sealed in between a moisture permeable sheet and a moisture impermeable sheet by bonding the four sides of the two sheets to make a bag. The moisture permeable sheet has a water vapor transmission rate of 5000 g/m²·24 hr as measured according to JIS Z0208 (hereinafter simply referred to as a moisture permeability). The bag containing the test piece is placed with the moisture permeable sheet side up in a 4.2-liter closed chamber having a relative humidity of 1% or lower while feeding 5.0 l/min of dry air into the chamber to induce heat generating reaction. The temperature of the lower side of the bag measured with a thermocouple is the temperature reached by the sheet on heat generation. The maximum temperature and the time required to reach the maximum temperature can arbitrarily be decided by the formulation of the components according to the purpose, that is, whether a steep temperature rise is desired or long duration of heat generating reaction at a relatively low temperature is desired, and the like.

It is desirable for the heat generating sheet 20 to generate 1 to 100 mg, particularly 1.0 to 50 mg, of water vapor per unit area (cm²) for 10 minutes. The amount of water vapor generated (mg/cm²·10 min) is measured, for example, as follows.

Measurement of Amount of Water Vapor Generated:

A heat generating sheet 20 having a prescribed size is allowed to stand in a 4.2-liter closed chamber having a relative humidity of 1% or less while feeding 2.1 l/min of dry air into the chamber and thus let to generate heat. The sheet was set in the chamber so that water vapor generated may dissipate in the chamber. The humidity of the air discharged from the chamber is measured with a hygrometer, from which the amount of water vapor generated per unit time after the start of heat generation is calculated according to equation (1) shown below. The cumulative amount of water vapor generated for a period of 10 minutes is obtained and converted to a value per unit area. In the following equations, e stands for water vapor pressure (pa); es, a saturated water vapor pressure (Pa; according to JIS Z8806); T, temperature (° C.; dry-bulb temperature); and s, sampling cycle (sec).

Relative humidity $U$ (% $RH$)=$(e/es)\times 100$

Absolute humidity $D$ $(g/m^3)=(0.794\times 10^{-2}\times e)/(1+0.00366T)=(0.794\times 10^{-2}\times U\times es)/[100\times(1+0.00366T)]$ Unit air volume $P$ (liter)=$(2.1\times s)/60$ Amount of water vapor per unit time $A$ $(g)=(P\times D)/1000$     (1)

Similarly to the time required for reaching the maximum temperature of heat generation, the amount of water vapor produced by the heat generating sheet 20 can be arbitrarily decided by the formulation of the components according to the purpose, that is, whether a steep temperature rise is desired or long duration of heat generating reaction at a relatively low temperature is desired, and the like.

As shown in FIG. 1, the holding member 3 has its periphery sealed to form a joint 30 with a prescribed width to have the heat generating sheet 20 enclosed therein. In the first embodiment, the joint 30 is formed by heat sealing.

The holding member 3 can be air permeable and capable of preventing the constituent components of the heat generating sheet 20 from falling off. To secure sufficient heat generating performance, the holding member 3 having a moisture permeability of 100 to 10000 g/m²·24 hr, particularly 1000 to 8000 g/m²·24 hr, is preferred. The holding member 3 may have air permeability in a part of, or the entire area thereof.

As shown in FIG. 2, the holding member 3 of the first embodiment has an air permeable sheet 31 and an air impermeable sheet 32 on the upper and the lower sides of the heat generating element 2, respectively. The warming device 1 of this embodiment has the air permeable sheet 31 disposed on the receiving part 5 side of the heat generating element 2 so that water vapor may dissipate into the receiving part 5. By this design, the warming device 1 exerts a humidifying function in the receiving part 5 as well as the heating function. When the heat generating mechanism is combined with any functional agent as hereinafter described, this design enhances penetration of the functional agent.

The holding member 3 of the warming device 1 according to the first embodiment has a three-layer structure on the receiving part 5 side (i.e., the upper side) of the heat generating element 2 and a four-layer structure on the opposite side (i.e., the lower side) of the heat generating element 2. The upper three-layer structure is composed of the air permeable sheet 31, a fibrous sheet 33 disposed on the lower side of the air permeable sheet 31, and a surfacing material 34 disposed on the upper side of the air permeable sheet 31. The lower four-layer structure is composed of two air impermeable sheets 32, a decorative sheet 35 disposed underneath the air impermeable sheets 32, and a surfacing material 36 disposed underneath the decorative sheet 35.

The air permeable sheet 31 can be of any sheet having air permeability. The air permeable sheet 31 preferably has a moisture permeability of 100 to 10000 g/m²·24 hr, particularly 1000 to 8000 g/m²·24 hr. The air permeable sheet 31 having such a moisture permeability allows the heat generating element 2 to generate heat and water vapor immediately after the warming device 1 is taken out the package. A wearer feels a part of his or her body warmed and moisturized. When the warming device 1 is used in combination with a functional agent, skin penetration of the functional agent can be enhanced. The air permeable sheet 31 may have air permeability in a part of or the entire area thereof.

The air permeable sheet 31 preferably has a basis weight of 10 to 200 g/m², particularly 20 to 100 g/m². The air permeable sheet 31 whose basis weight is in this range is thin and flexible, feels very comfortable to wear, and causes neither impairment of the softness of the heat generating element 2 nor hindrance to immediate heat and water vapor generation.

The air permeable sheet 31 includes a mechanically perforated sheet of a resin, such as polyolefin (e.g., polyethylene or polypropylene), polyester, polyamide, polyurethane, polystyrene or an ethylene-vinyl acetate copolymer; a microporous sheet obtained by stretching a sheet having inorganic filler particles dispersed in the above-recited resin matrix or by making an use of interfacial separation of the crystal structure; and an open-cell sheet formed by expansion molding. Nonwoven or woven fabrics made of synthetic fibers (e.g., polyolefin fiber), wood pulp or semi-synthetic fibers (e.g., rayon and cellulose acetate), vinylon fiber, polyester fiber, etc., synthetic paper, and paper are also useful. A stack of a few air-permeable sheets 31 may also be used.

The air impermeable sheet 32 can be of any material. The air impermeable sheet 32 preferably has a moisture permeability of 10 g/m²·24 hr or less, particularly 1.0 g/m²·24 hr or less. The moisture permeability of the air impermeable sheet 32 falling within this range, the direction of water vapor's dissipation can be controlled. That is, oxygen is supplied to the heat generating element 2 only from the air permeable sheet side, and water vapor generated on oxidation is released only from the air permeable sheet side while preventing water vapor dissipation from the air impermeable sheet side.

The air impermeable sheet 32 preferably has a basis weight of 10 to 200 g/m², particularly 20 to 100 g/m². Within this range of basis weight, the air impermeable sheet 32 is capable of regulating the direction of water vapor dissipation and hiding the heat generating element while maintaining softness and flexibility of the warming device 1.

Materials of the air impermeable sheet 32 include polyolefin (e.g., polyethylene and polypropylene), polyester, polyamide, polyurethane, polystyrene, nylon, polyvinylidene chloride, and an ethylene-vinyl acetate copolymer. Where the air impermeable sheet 32 is required to hide the heat generating element 2 from the sight, a sheet made of the above-recited resin having an inorganic filler (e.g., titanium oxide) dispersed therein is effective. While the warming device 1 shown in FIG. 2 has two air impermeable sheets 32, only one sheet will do, or more than two sheets may be stacked.

The warming device 1 has a fibrous sheet 33 between the air permeable sheet 31 and the heat generating sheet 20. The fibrous sheet 33 is effective in stopping expansion of the holding member accompanying water vapor generation and preventing separation and fall-off of the oxidizable metal, the moisture retaining agent, etc. without hindering effective generation of water vapor. It is preferred for the fibrous sheet 33 to have a moisture permeability of 1000 g/m²·24 hr or more, particularly 2000 g/m²·24 hr or more. The moisture permeability of the surface material falling within this range, the percolation of oxygen is not prevented and a good heat generation occurs.

It is preferred for the fibrous sheet 33 to have a prescribed breaking extension as well as air permeability. Specifically, the fibrous sheet 33 preferably has a breaking extension of 0.1 to 10%, particularly 1.0 to 5.0%. Within this range of breaking extension, the fibrous sheet 33 is capable of stopping expansion of the holding member 3 accompanying water vaporization.

The fibrous sheet 33 preferably has a basis weight of 10 to 200 g/m², particularly 20 to 100 g/m². Within this range of basis weight, the fibrous sheet 33 suppresses expansion of the holding member 3 while ensuring effective water vaporization without impairing thinness, flexibility and good feel of the heat generating main body 4 and softness of the heat generating element 2.

The fibrous sheet 33 includes nonwoven or woven fabrics made of synthetic pulp(e.g., polyolefin pulp), wood pulp, semi-synthetic fibers (e.g., rayon and cellulose acetate) or synthetic fibers (e.g., vinylon fiber and polyester fiber), synthetic paper, and paper. A stack of a few fibrous sheets 33 may also be used.

The warming device 1 has a surfacing material 34 on the upper side of the air permeable sheet 31. The surfacing material 34 not only gives a wearer an improved feel to the touch but is effective in relaxing heat conduction. It is possible to apply a drug to the surfacing material 34 by impregnation or coating so that the drug may penetrate into the skin effectively.

The surfacing material 34 can be of any material having a good texture and flexibility. The thickness of the surfacing material 34 is preferably 0.1 to 2.0 mm, more preferably 0.2 to 1.0 mm. Within this thickness range, the surfacing material 34 is effective in relaxing the heat of the heat generating element to give a mild warm feel. It is preferred for the surface material 34 to have a moisture permeability of 1000 g/m²·24 hr or more, particularly 2000 g/m²·24 hr or more. The moisture permeability of the surface material falling within this range, the percolation of oxygen is not prevented and a good heat generation occurs.

The basis weight of the surfacing material 34 preferably ranges from 5.0 to 200 g/m², particularly 10 to 100 g/m². The surfacing material 34 with a basis weight less than 5.0 g/m² is liable to break due to insufficient strength. The surfacing material 34 with a basis weight more than 200 g/m² tends to feel rough or act as a heat insulator hindering heat conduction.

The surfacing material 34 can be made of nonwoven fabrics of synthetic fibers, such as polyolefin (e.g., polyethylene or polypropylene), polyester (e.g., polyethylene terephthalate), polyamide, polyurethane, polystyrene, and ethylene-vinyl acetate copolymers, plant fibers, such as cotton and hemp, animal fibers, such as wool and silk, regenerated fibers, such as rayon and cuprammonium rayon, or semi-synthetic fibers, such as cellulose acetate; traditional Japanese paper; paper; synthetic paper; woven fabrics (e.g., woolen fabric); leather; and the like. A stack of two or more surfacing materials 34 may be used.

The warming device 1 has a decorative sheet 35 underneath the air impermeable sheets 32. The decorative sheet 35 is effective in hiding the heat generating element 2 from the sight. The decorative sheet 35, printed or colored, enhances the appearance of the warming device.

Any air impermeable sheet can be used as a decorative sheet 35. It is preferred for the decorative sheet 35 to have moisture permeability of 10 g/m²·24 hr or less, particularly 1.0 g/m²·24 hr or less. The moisture permeability of the decorative sheet 35 falling within this range, the direction of water vapor's dissipation can be controlled. That is, oxygen is supplied to the heat generating element 2 only from the air permeable sheet side, and water vapor generated on oxidation is released only from the air permeable sheet side while preventing water vapor dissipation from the air impermeable sheet side.

The decorative sheet 35 preferably has a basis weight of 10 to 200 g/m², particularly 20 to 100 g/m². Within this range of basis weight, the decorative sheet 35 is capable of regulating the direction of water vapor dissipation and exhibits improved hiding properties while retaining softness and flexibility of the warming device.

The decorative sheet 35 includes sheets made of polyolefin (e.g., polyethylene or polypropylene), polyester, polyamide, polyurethane, polystyrene, nylon, polyvinylidene chloride, ethylene-vinyl acetate copolymers, etc. Where heat generating element hiding properties are demanded, in particular, a sheet of the above-recited resin having an inorganic filler (e.g., titanium oxide) dispersed therein is preferred. A stack of two or more decorative sheets 35 can be used.

The surfacing material 36 disposed on the decorative sheet 35 as the undermost layer is the same as the surfacing material 34.

While the warming device 1 of the first embodiment has two air permeable sheets of different kinds (i.e., sheets 31 and 33), only one air permeable sheet will do seeing that the components of the heat generating element 2 are far less liable to fall off than conventional heat generating elements of powder form. Two or more air permeable sheets of a kind can be used as well. While the warming device 1 has air impermeable sheets of different kinds (sheets 32 and 35), only one air impermeable sheet will do where hiding properties and decorative design are not so necessary. In this way reduction of the number of constituent layers will make the warming device thinner, more flexible, and more competitive in price.

The holding member 3 has its periphery heat-sealed with the heat generating sheet 20 enclosed therein to make the heat generating main body 4.

The heat generating main body 4 preferably has a thickness of 0.1 to 3 mm, particularly 0.3 to 1.5 mm, and a basis weight of 100 to 6000 g/m², particularly 200 to 3000 g/m², so as to provide a warming device that is thin, flexible, and conformable to a part of a body.

It is desirable for the warming device 1 or the heat generating main body 4 to generate 0.1 to 100 mg/cm²·10 min, preferably 1.0 to 50 mg/cm²·10 min, of water vapor. The amount of water vapor generated from the warming device or the heat generating main body (mg/cm²·10 min) is measured in the same manner as for the measurement of the amount of water vapor generated from the heat generating sheet. In this case the amount of water vapor is measured where the warming device or the heat generating main body itself is placed in the measurement system.

Similarly to the time required to reach the maximum temperature, the amount of water vapor produced by the heat generating main body 4 can be arbitrarily designed by the formulation of the components and the layer structure according to the purpose, for example, depending on whether a steep temperature rise is desired or long duration of heat generating reaction at a relatively low temperature is desired.

The receiving part-forming member 6 of the warming device 1 according to the first embodiment has a three-layer structure consisting of an air permeable sheet 61, a surfacing material 60 disposed on one side of the air permeable sheet 61, and a surfacing material 62 disposed on the other side of the air permeable sheet 61. Having the air permeable sheet 61, the receiving part-forming member 6 supplies oxygen to the heat generating element 2 smoothly thereby letting the heat generating element 2 rapidly generate heat and a large quantity of water vapor.

The air permeable sheet 61 can be the same as the air permeable sheet 31. The surfacing materials 60 and 62 can be the same as the surfacing material 34.

The receiving part-forming member 6 are joined to the heat generating main body 4 through heat sealing in such a configuration as to form an insertion opening 50 and the receiving part 5. The joint may be discontinuous at an arbitrary interval so as to smoothen oxygen supply.

The warming device 1 preferably has a thickness of 0.2 to 5 mm, particularly 0.5 to 3 mm, to give a user convenience and comfort, i.e., portability (thinness and ease of folding), softness, flexibility, and conformability to any part of a user's body, such as the head, the face, hands, feet, etc.

The maximum temperature reached by the warming device 1 or the heat generating main body 4 on heat generation is preferably 30 to 100° C., more preferably 35 to 60° C. This temperature is measured as follows.

Measurement of Maximum Temperature Reached by Warming Device on Heat Generation:

The warming device 1 or the heat generating main body 4 is placed with its air permeable sheet side up in a 4.2-liter closed chamber having a relative humidity of 1% or lower while feeding 5.0 l/min of dry air into the chamber to induce heat generating reaction. The temperature of the lower side of the laminate measured with a thermocouple is the temperature reached by the warming device. The maximum temperature can also be measured according to the temperature property measurement of the disposable body warmers of JIS S4100. The maximum temperature to be reached by the warming device can arbitrarily be set by the formulation of the components and the layer structure according to the purpose, for example, depending on whether a steep temperature rise is desired or long duration of heat generating reaction at a relatively low temperature is desired.

The warming device 1 can be produced by, for example, interposing a heat generating sheet 20, which is prepared as described below, at a prescribed position between upper and lower sheets making up the holding member 3, fixing the periphery or one side of the heat generating sheet 20 to the lower sheet by heat sealing or with an adhesive, bonding the periphery of all the upper and lower sheets to enclose the heat generating sheet 20 therebetween, cutting the laminate into a prescribed shape to form a heat generating main body 4, and bonding the receiving part-forming member 6 with the heat generating main body 4. The receiving part-forming member 6 may be bonded simultaneously with bonding the periphery of the sheets making up the heat generating main body 4.

Production of the heat generating sheet 20 starts with preparation of a raw material composition (slurry) comprising water, the oxidizable metal, the moisture-retaining agent, the fibrous material, and necessary additives, preferably a flocculant.

Flocculants which can be used in the present invention include inorganic ones, such as metal salts, e.g., ammonium sulfate, polyaluminum chloride, ferric chloride, polyferric sulfate, and ferrous sulfate; polymeric ones, such as polyacrylamides, sodium polyacrylates, Mannich base-modified polyacrylamide, aminoalkyl poly(meth)acrylates, sodium carboxymethyl celluloses, chitosans, starches, and polyamide-epichlorohydrins; organic flocculants, such as dimethyldiallylammonium chloride type or ethyleneimine type alkylene dichloride-polyalkylenepolyamine condensates, and dicyandiamide-formalin condensates; clay minerals, such as montmorillonite and bentonite; silicon dioxide and its hydrates, such as colloidal silica; and hydrous magnesium silicate, such as talc. Preferred of these flocculants are combinations of an anionic agent and a cationic agent from the standpoint of sheet surface properties, formation, molding properties, powder fixing properties, and sheet strength. Suitable combinations include a combination of colloidal silica or bentonite (anionic) and starch or polyacrylamide (cationic) and a combination of sodium carboxymethyl cellulose (anionic) and a polyamide-epichlorohydrin resin (cationic). In addition to these combinations, the above-recited flocculants can be used either individually or in combination of two or more thereof.

The flocculant is preferably used in an amount of 0.01 to 5% by weight, particularly 0.05 to 1% by weight, based on the total solids content of the slurry. The amount of 0.01% by weight or more of the flocculant based on the total solids content of the slurry has good flocculating effect that the components such as the oxidizable metal and the moisture retaining agent tend to be retained in the papermaking step and that the slurry tends to have uniform composition and can provide a sheet with a uniform thickness and a uniform composition. The amount of 5% by weight or less of the flocculant based on the total solids content of the slurry prevents a sticking to drying rolls in the step of sheet drying or prevents a main cause of breaking or scorching, resulting in good productivity. The flocculant in such a amount tends to keep the potential balance of the slurry, which results in preventing from fall off of the particulate or fibrous components into white water during papermaking. Moreover, oxidation may be suppressed in the sheet, resulting in good storage stability of heat generating performance and strength.

The slurry concentration preferably ranges 0.05 to 10% by weight, particularly 0.1 to 2% by weight. Where the concentration is 0.05% by weight or more, a large quantity of water and much time are not required to form a sheet with a uniform thickness in papermaking process. Where the concentration is 10% by weight or less, the components sufficiently disperse in the slurry to provide a sheet with good surface properties or a uniform thickness.

The slurry is made into a sheet by papermaking techniques. Papermaking techniques include continuous papermaking by use of a cylinder paper machine, a foundrinier paper machine, Yankee paper machine, a twin-wire paper machine, etc.; and batch papermaking such as manual papermaking. A multilayer sheet may be made by successively using slurries of different formulations or laminating sheets separately prepared from slurries of different formulations.

The wet sheet prepared by papermaking is dewatered preferably to a water content of 70% by weight or less, particularly 60% by weight or less, for assuring shape retention and mechanical strength. Dewatering is carried out by, for example, suction, application of pressurized air or pressing with a pressure roll or a pressure plate.

The dewatered sheet, which contains the oxidizable metal capable of exothermic reaction in an ordinary atmosphere, is then subjected to positive drying to remove the water content thereby providing a heat generating sheet which is inhibited from inducing oxidation of the oxidizable metal during the subsequent fabrication steps and has excellent long-term storage stability. Drying of the sheet is preferably carried out before addition of the aforementioned electrolyte (application of an electrolytic solution) so that the oxidizable metal may be firmly fixed and held by the fibrous material and be prevented from falling off and that mechanical strength improvement by addition of a heat fusible component, a thermal crosslinking component or a aqueous component may be expected.

The heat fusible component includes such as high-density polyethylene, medium-density polyethylene, low-density polyethylene, polypropylene, polyester, polyvinylidene chloride, polyvinyl alcohol, polyvinyl acetate, or a copolymer comprising monomers of these homopolymers.

The thermal crosslinking component includes phenolic resin; epoxy resin; urea resin; furan resin; polyurethan; amino resins such as melamine; unsaturated polyester resin; diallyl phthalate resin and the like.

The aqueous component includes natural polymers such as starch, guar gum, carboxymethyl cellulose; natural aqueous polymers such as polyvinyl alcohol, polyacrylamide, polyacrylamide and the like.

The sheet is preferably dried by heating. The heating temperature is preferably 60 to 300° C., more preferably 80 to 250° C. If the heat drying temperature is too low, the drying time must be extended, which may accelerate oxidation of the oxidizable metal, resulting in reduction of heat generating performance of the sheet. Accelerated oxidation of the oxidizable metal in the vicinities of the upper and lower sheet surfaces sometimes results in color change to pale brown. Too high a drying temperature invites not only deterioration in performance of the moisture-retaining agent, etc., which results in reduction of heat generating performance of the heat generating sheet, but also abrupt water vaporization inside the sheet, which can destroy the sheet structure.

The drying is preferably effected to reduce the water content to 20% by weight or less, particularly 10% by weight or less. Where the residual water content is 20% by weight or less, the resulting sheet has good long-term storage stability. For example, when the sheet is stored in a roll form, water may not migrate in the radial direction of the roll, resulting in variations of heat generating performance and mechanical strength.

The method of drying is selected appropriately depending on the sheet thickness, the treatment given to the sheet before drying, the water contents before and after the drying, and the like. Useful drying methods include contact with a heating unit, application of heated air or steam (superheated steam), vacuum drying, microwave heating, and electric current heating. The drying may be carried out simultaneously with the above-described dewatering.

The shaping of the wet sheet including dewatering and drying is preferably conducted in an inert gas atmosphere. Where the sheet to be shaped is free from an electrolyte that acts as an oxidation promoter, the shaping may be performed in an ordinary air atmosphere if desired, which enables simplification of equipment. Where necessary, the dried sheet is fabricated by craping, slitting, trimming or any other processes for shaping or forming. Thin and yet tearproof, the resulting sheet can be taken up in a roll. The sheet or a plurality of the sheets may be pressed either alone or as laminated with other film or sheet (e.g., paper, woven fabric, nonwoven fabric or plastic film). The plurality of the sheets and optionally the other film or sheet may be united into an integral sheet, given uneven patterns or perforated by pressing, embossing or needle punching. In order to facilitate laminating by heat sealing, a thermoplastic resin component or a hot-water-soluble component may be incorporated into the slurry.

The electrolyte is then incorporated into the sheet. This step is preferably carried out in an inert gas atmosphere such as nitrogen or argon. Where the electrolyte is incorporated by impregnation with an electrolytic solution, the impregnating step may be conducted in an ordinary air atmosphere because oxidation that may proceed immediately after impregnation is mild. The electrolyte to be incorporated is the same as used in the heat generating sheet.

The method for incorporating the electrolyte into the sheet is selected appropriately according to the treatment given to the sheet after papermaking, the water content and the form (e.g., thickness) of the sheet, and the like. For example, the electrolyte can be incorporated by impregnating the sheet with an electrolytic solution having a prescribed electrolyte concentration or adding a powdered electrolyte having a prescribed particle size directly to the sheet. Impregnation is preferred for achieving uniform distribution of the electrolyte and simultaneously controlling the water content of the resulting sheet.

The manner of impregnation is chosen according to the form (e.g., thickness) and the water content of the sheet, and the like. Impregnation methods include spraying, syringing into part of the sheet (the injected electrolytic solution penetrates throughout the sheet by capillarity), coating with a brush, etc., soaking in the electrolytic solution, gravure coating, reverse coating, doctor blade coating, and so forth. Spraying is preferred for uniform distribution, ease of operation, and relatively low cost of equipment. Where the finished product has a complicated shape or layer structure, syringing is preferred for productivity, process flexibility (the final finishing process can be done in a separate step), and simplicity of equipment. It is possible to conduct syringing after the sheet is enclosed in the holding member.

If necessary, the water content of the sheet containing the electrolyte is adjusted to render the heat generating sheet stable against storage. The heat generating sheet thus prepared can be fabricated by trimming into a prescribed size or superposed one on another.

Figure 3:
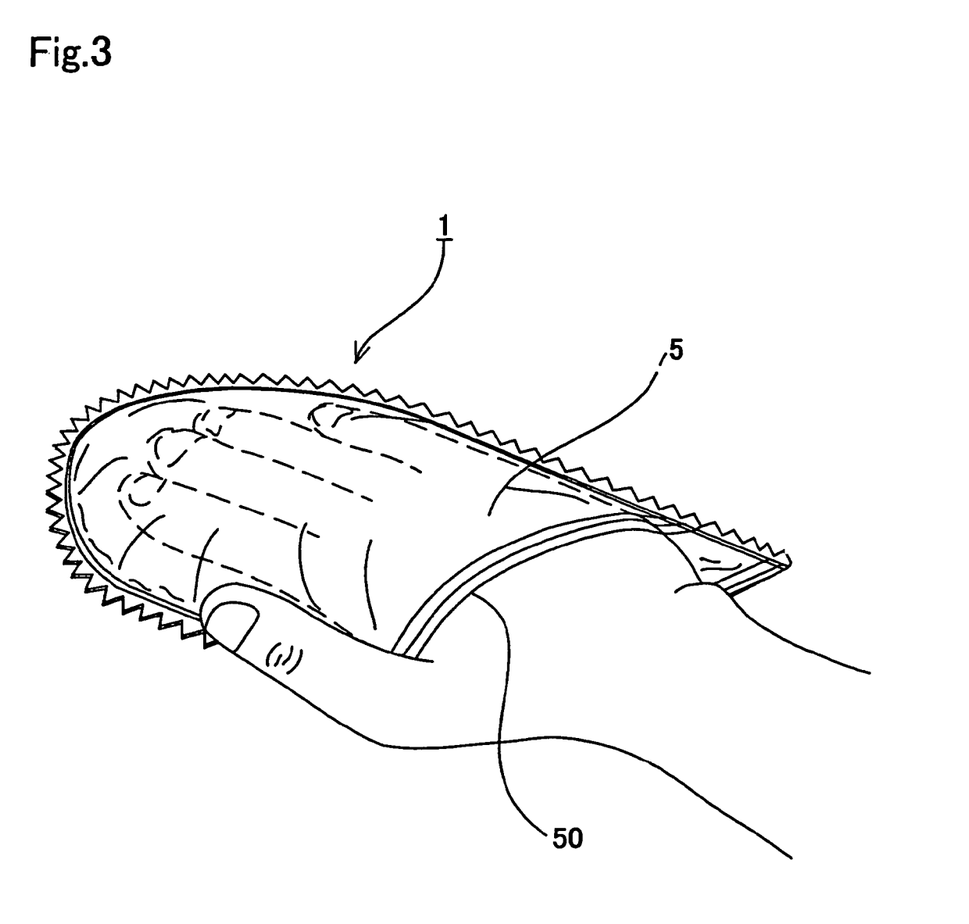
FIG. 3 is a perspective showing use of the warming device of the first embodiment.

The warming device 1 is supplied as sealed in an air impermeable package until use. On use, a hand is inserted through the opening 50 into the receiving part 5 as illustrated in FIG. 3. The oxidizable metal of the heat generating sheets 20 undergoes oxidation to generate heat to warm the receiving part 5, and water vapor is generated by the heat to humidify the receiving part 5.

The warming device 1 of the first embodiment is thin, flexible, and conformable to the hand inserted. The warming device 1 is capable of not only warming the hand with the heat generated by oxidation of the oxidizable metal but moisturizing the hand by the water vapor generated by the heat and dissipated in the receiving part 5. The warming device 1 enjoys a diversity of uses by taking advantage of the warming and moisturizing effects combined with the function of a functional agent. For instance, a functional agent is previously applied to the part of a body to be warmed or a layer (e.g., nonwoven fabric) to be brought into contact with the part of a body by impregnation. In this case, the warming device 1 helps the functional agent penetrate through the skin. When combined with hot packs or cataplasm, the warming device 1 is also useful for skin care (for moisturizing, wrinkle reduction, etc.) or health care (for pain alleviation, etc.). Since the warming device 1 is capable of moisturizing as well as warming, such a functional agent, when combined with the warming device 1, is made very effective thanks to penetration aided by the heat and moisture.

Other embodiments of the warming device according to the present invention will be described by referring to FIGS. 4 through 6, in which the same elements or members as in the first embodiment are indicated by the same numbers used in FIGS. 1 to 3. The foregoing description of the first embodiment applies to those particulars not referred to in what follows.

Figure 4:
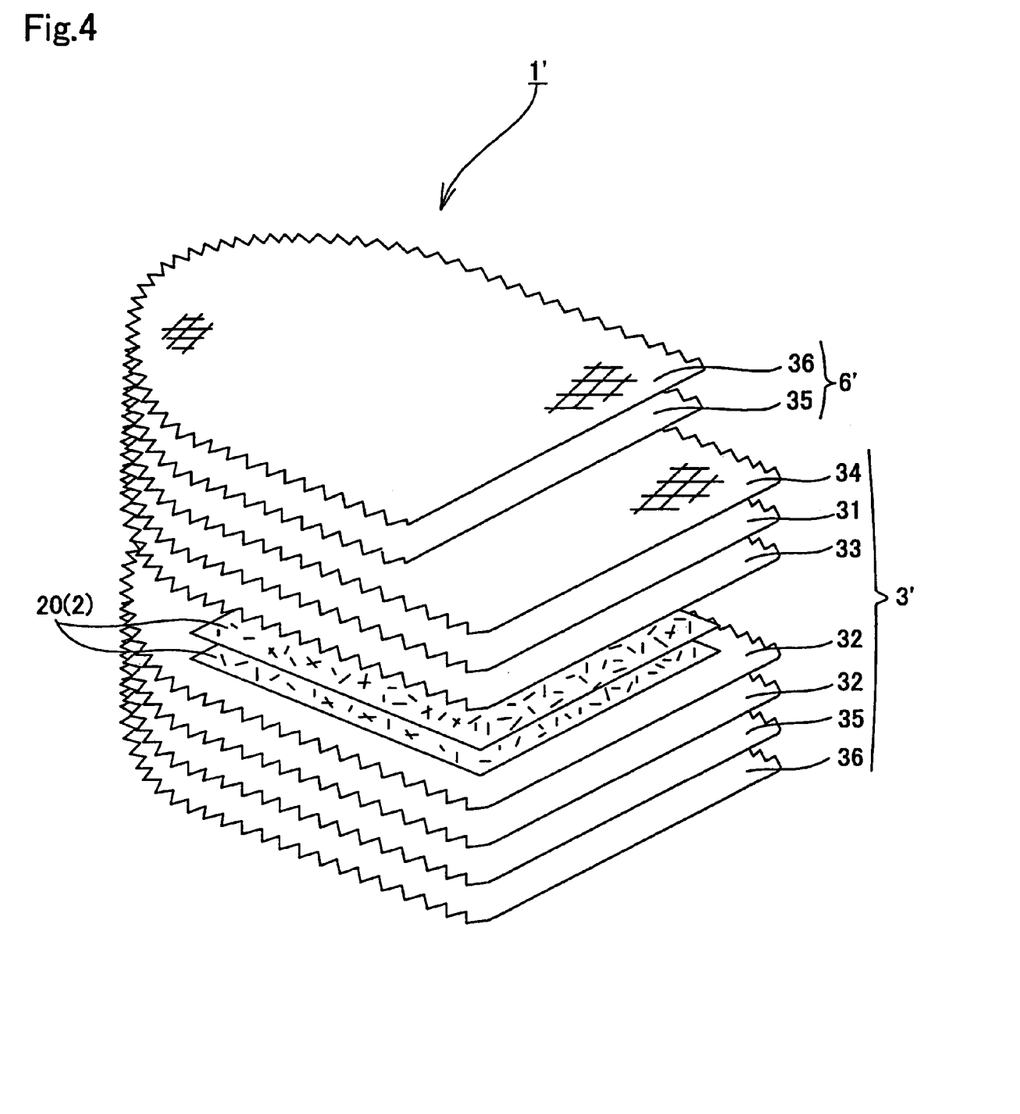
FIG. 4 is an exploded perspective schematically illustrating a second embodiment of the warming device according to the present invention.

FIG. 4 is an exploded perspective of the second embodiment. The warming device 1' according to the second embodiment has the same layer structure as the warming device 1 except that the receiving part-forming member 6' of the device 1' has a two-layer structure consisting of the decorative sheet 35 and the surfacing material 36 superposed on the outer side of the decorative sheet 35.

By virtue of this structure of the receiving part-forming member 6', the warming device 1' is capable of retaining more water vapor within the receiving part 5, to say nothing of the same effects as produced by the warming device 1. In addition, the warming device 1' shows a milder rise of temperature to give gentle warming and moisturizing feel and has a long duration.

Figure 5:
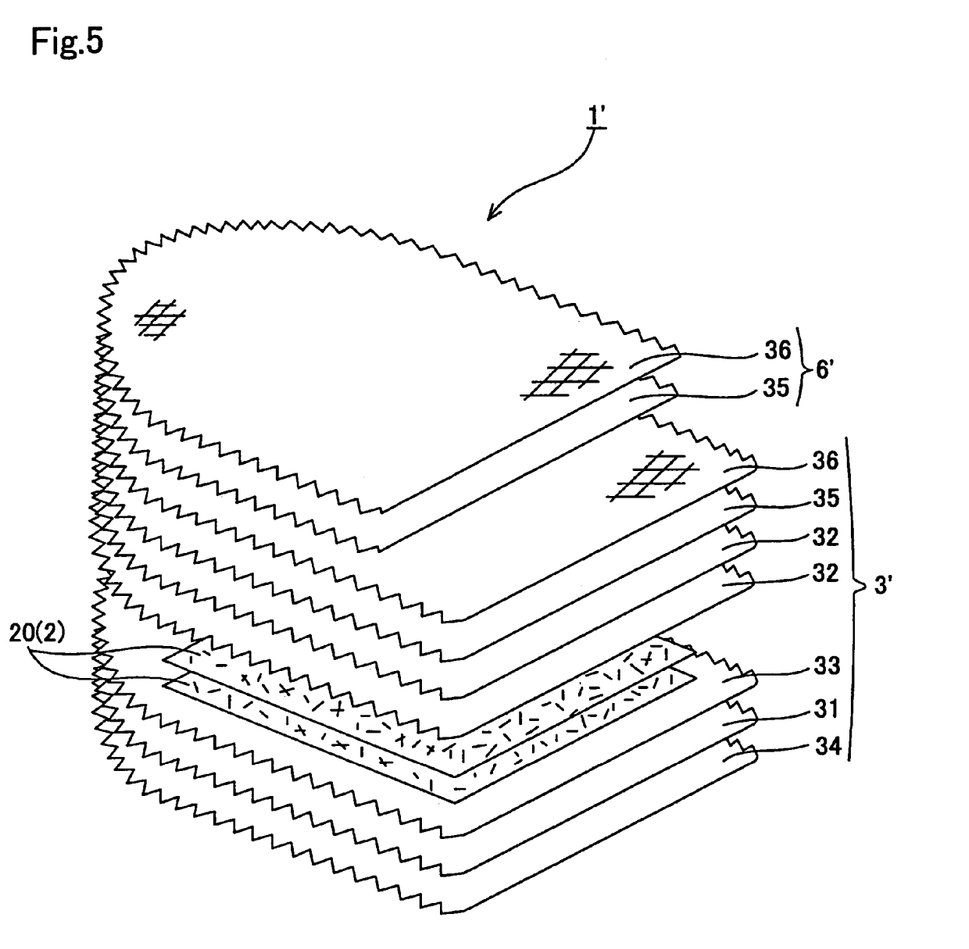
FIG. 5 is an exploded perspective schematically illustrating a third embodiment of the warming device according to the present invention.

FIG. 5 is an exploded perspective of the third embodiment. The warming device 1' of the third embodiment has the same layer structure as the second embodiment, except the layer structures on both sides of the heat generating main body 4 are reversed and that the receiving part-forming member 6' is bonded to the surfacing material 36.

The warming device 1' of this embodiment has air permeability on its lower side (as depicted in FIG. 5) opposite to the receiving part 5 side. Therefore, water vapor is hardly dissipated into the receiving part 5. With this air permeable side faced to or brought into contact with an object to be warmed, the warming device 1' exerts its warming and humidifying effects toward the object. The warming device 1' is suitable as a hot sheet combined with various functional preparations for, for example, cleaning, sterilization, slow wax release, scenting or deodorization, in house care applications (cleaning or treatment of flooring, tatami, kitchen stoves and fans, etc.), air care applications to create a particular ambiance, car care applications (cleaning and waxing), and facial and body skin care applications (cleansing, sterilizing, moisturizing, and make-up removal). When combined with a pack, the warming device 1' provides a skin-care hot pack for moisturizing, and eliminating darkness under the eye, wrinkles or skin dullness or an eye-care hot pack for improving eyesight. When combined with cataplasm, the warming device 1' provides health-care hot cataplasm for alleviating pains in the neck, shoulders, feet, the lower back, etc. or period pains.

Figure 6A:
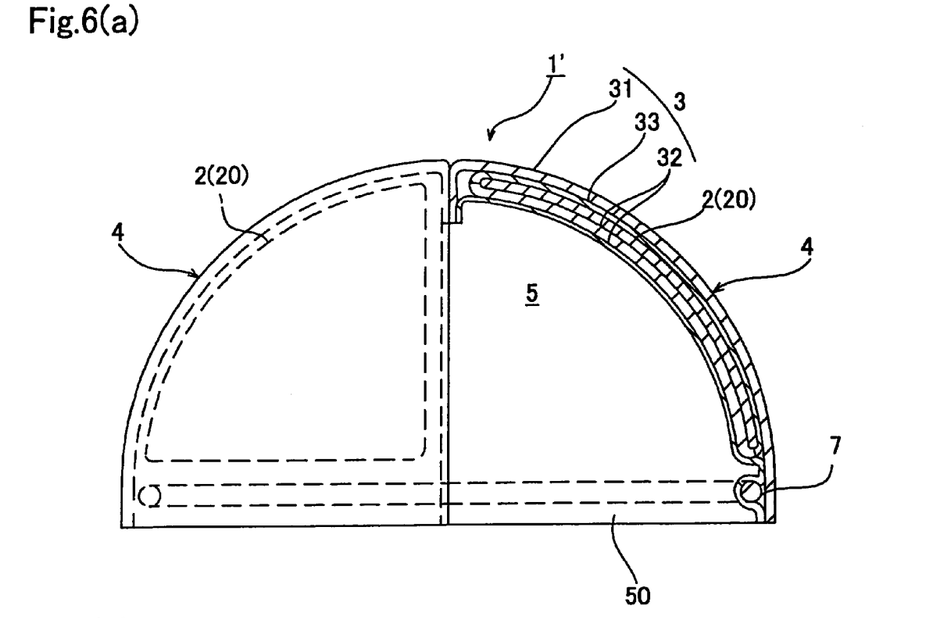
Figure 6B:
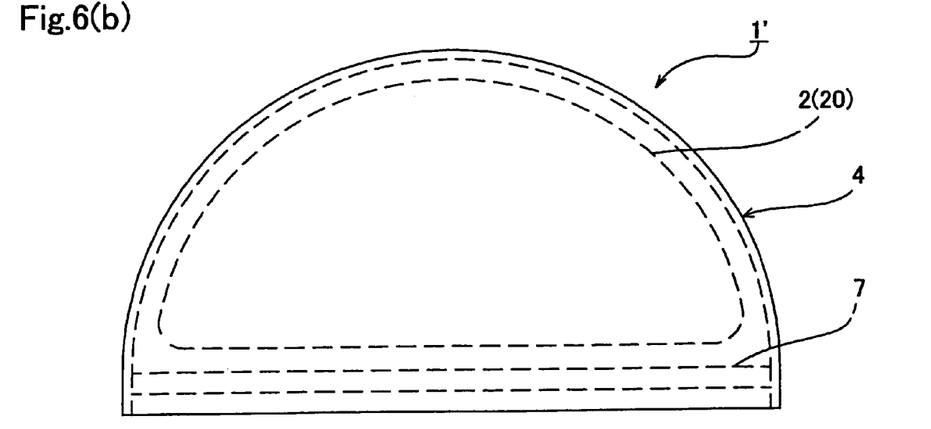

FIGS. 6(*a*) and 6(*b*) schematically show the fourth embodiment. The warming device 1' of the fourth embodiment has a cap shape having the receiving part 5 in which the head of a user is fitted. The warming device 1' is equipped with a pursing member 7 by which the insertion opening 50 can be pursed to fit to the head.

A pair of heat generating main bodies 4 each having a semicircular shape are joined at their semi-circular peripheries to make a cap with the opening 50 and the receiving part 5.

Each of the heat generating main bodies 4 is composed of the holding member 3 and the semi-circular heat generating element 2 enveloped and sealed in the holding member 3. The heat generating element 2 is sealed in between a fibrous sheet 33 and an air impermeable sheet 32 that are disposed on the outer side and the inner side of the heat generating element 2, respectively. An air permeable sheet 31 is superposed on the fibrous sheet 33, and another air impermeable sheet 32 is superposed on the exterior side of the air impermeable sheet 32.

The pursing member 7 is arranged along the opening 50 between the air permeable sheet 31 and the exterior air impermeable sheet 32. The pursing member 7 used in this particular embodiment is an elastic band which is held to go round the opening 50. Other known means for pursing, such as a drawstring and a mechanical fastener, can be used as a pursing member.

Figure 7:
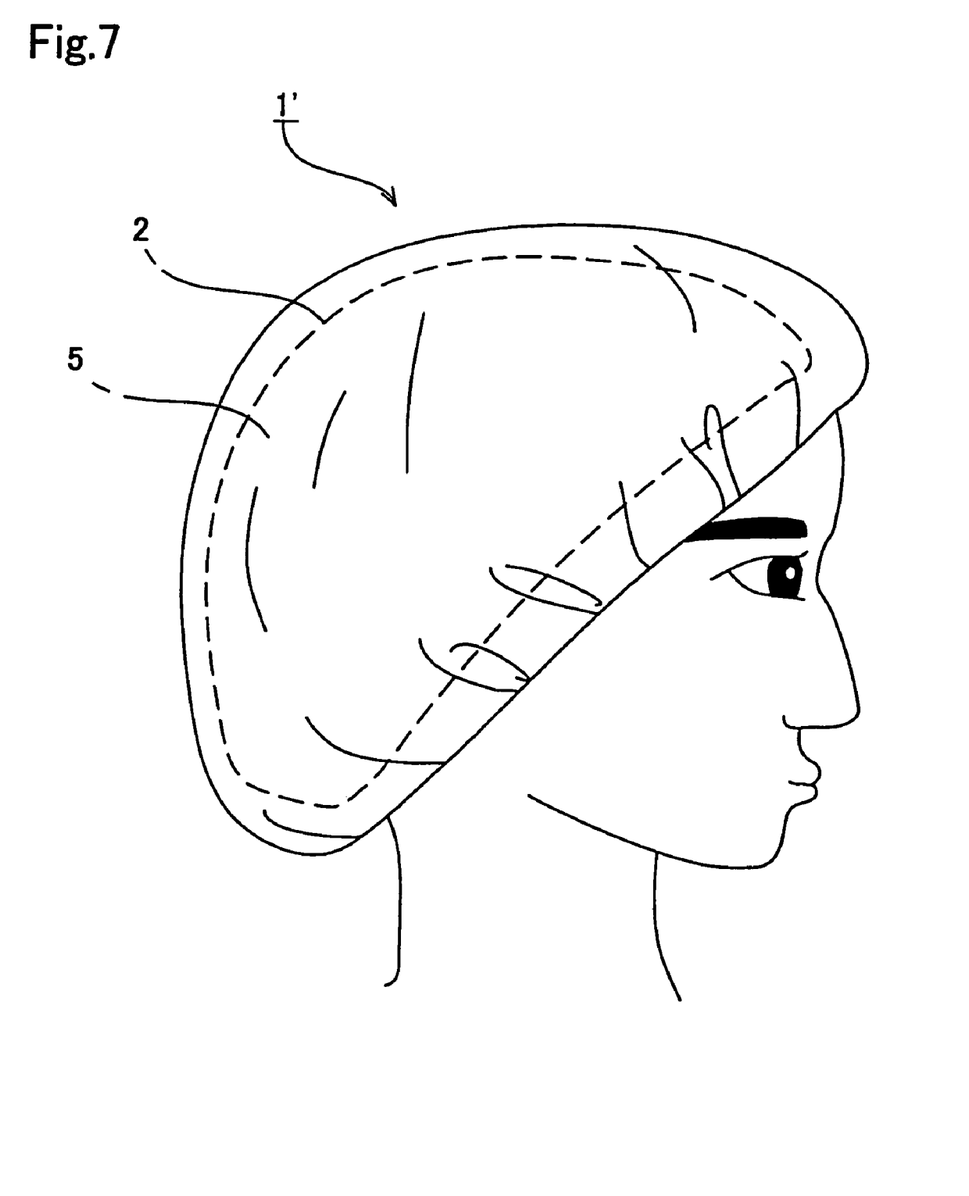
FIG. 7 is a side view illustrating the warming device of the fourth embodiment while in use.

In using the warming device 1' of the fourth embodiment, it is put on the head as shown in FIG. 7, and the head is warmed by the heat generated on oxidation of the oxidizable metal of the heat generating element 2.

The warming device 1' of the fourth embodiment is thin, flexible, and conformable to the shape of the head. It is suitable as a warming cap in, for example, hair care applications in perming, hair dyeing, hair treatment, and the like.

The present invention is not construed as being limited to the above-described embodiments, and various changes and modifications can be made therein without departing from the spirit and scope thereof.

The following modifications are included under the scope of the present invention. The layer structures of the heat generating element, the holding member, and the receiving part-forming member are subject to variation according to the purpose. For example, the heat generating main body may be adapted to dissipate water vapor from both sides thereof whereas the one according to any of the aforementioned embodiments is designed to dissipate water vapor only from its air permeable side.

While in the foregoing embodiments the holding member 3 has a multilayer structure, it may have a single layer structure as far as it possesses air permeability enough to cause oxidation and prevents particulate or fibrous components of the heat generating element from falling off.

Sealing the holding member and joining the holding member and the receiving part-forming member may be carried out by any means other than heat sealing adopted in the foregoing embodiments, such as bonding with an adhesive or stitching together.

The receiving part of the warming device according to the present invention can be designed in conformity to various parts of a body, such as a foot or an ear, as well as a hand or the head as in the above embodiments.

The present invention provides a warming device that is thin, flexible, conformable to a part of a body, and suitable to a variety of applications.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A warming device comprising a heat generating main body comprising:
    a heat generating element;
    an air-permeable holding member including the heat generating element enclosed therein; and
    a receiving part configured to receive a part of a body being inserted, the heat generating element comprising a heat generating sheet which is prepared by papermaking,
    wherein an interior surface of said receiving part is formed by an exterior surface of said air-permeable holding member,
    the sheet contains 50% by weight or more of components other than fibrous material and contains a fibrous material including a CSF of 600 ml or less, and the air-permeable holding member includes:
    a first air impermeable layer disposed on first side of the heat generating element and adjacent to the heat generating element,
    a second air impermeable layer disposed on the first side of the heat generating element and adjacent to the first air impermeable layer,
    a fibrous layer disposed on a second side of the heat generating element, which is an opposite side of the heat generating element from the first side, and
    an air permeable layer disposed on the second side of the heat generating element adjacent to the fibrous layer.

2. The warming device according to claim 1, wherein the sheet has a thickness of 0.1 to 2.0 mm.

3. The warming device according to claim 1, wherein the heat generating main body generates 0.1 to 100 mg/cm$^2 \cdot$10 mm of water vapor.

4. The warming device according to claim 1, wherein receiving part is formed on the outer side of the heat generating main body.

5. The warming device according to claim 1, wherein the fibrous material has a negative zeta potential.

6. A warming device comprising a heat generating main body comprising:
    a heat generating element;
    an air-permeable holding member including the heat generating element enclosed therein; and
    a receiving part configured to receive a part of a body being inserted, the heat generating element comprising a heat generating sheet which is prepared by papermaking,
    wherein an interior surface of said receiving part is formed by an exterior surface of said air-permeable holding member,
    the receiving part has a first side adjacent to the heat generating sheet and a second side opposite the first side across a gap of the receiving part, and
    the air-permeable holding member includes:
    a first air impermeable layer disposed on first side of the heat generating element and adjacent to the heat generating element,
    a second air impermeable layer disposed on the first side of the heat generating element and adjacent to the first air impermeable layer,
    a fibrous layer disposed on a second side of the heat generating element, which is an opposite side of the heat generating element from the first side, and
    an air permeable layer disposed on the second side of the heat generating element adjacent to the fibrous layer.

7. The warming device according to claim 6, which is configured to dissipate water vapor inside the receiving part.

8. The warming device according to claim 6, wherein the second side of the receiving part includes two surfacing material layers and an air-permeable layer disposed between the two surfacing material layers.

9. The warming device according to claim 8, wherein the second air impermeable layer is configured to retain a pursing member.

* * * * *